US007461045B1

(12) United States Patent
Chaovalitwongse et al.

(10) Patent No.: US 7,461,045 B1
(45) Date of Patent: Dec. 2, 2008

(54) OPTIMIZATION OF SPATIO-TEMPORAL PATTERN PROCESSING FOR SEIZURE WARNING AND PREDICTION

(75) Inventors: Wanpracha A. Chaovalitwongse, Hillsborough, NJ (US); Leonidas D. Iasemidis, Scottsdale, AZ (US); Panos M. Pardalos, Gainesville, FL (US); James C. Sackellares, Gainesville, FL (US); Deng-Shan Shiau, Gainesville, FL (US)

(73) Assignees: University of Florida Research Foundation, Inc., Gainesville, FL (US); Arizona Board of Regents, Scottsdale, AZ (US)

( * ) Notice: Subject to any disclaimer, the term of this patent is extended or adjusted under 35 U.S.C. 154(b) by 581 days.

(21) Appl. No.: 10/920,446

(22) Filed: Aug. 18, 2004

Related U.S. Application Data

(60) Provisional application No. 60/495,702, filed on Aug. 18, 2003.

(51) Int. Cl.
  *G06F 9/44* (2006.01)
  *G06N 7/02* (2006.01)
  *G06N 7/06* (2006.01)
(52) U.S. Cl. ............................................. 706/52
(58) Field of Classification Search ............... None
  See application file for complete search history.

(56) References Cited

U.S. PATENT DOCUMENTS

| | | | | |
|---|---|---|---|---|
| 5,995,868 | A * | 11/1999 | Dorfmeister et al. | 600/544 |
| 6,167,360 | A * | 12/2000 | Erickson et al. | 703/6 |
| 6,304,775 | B1 * | 10/2001 | Iasemidis et al. | 600/544 |
| 6,466,822 | B1 * | 10/2002 | Pless | 607/45 |
| 6,529,774 | B1 * | 3/2003 | Greene | 600/545 |
| 6,549,804 | B1 * | 4/2003 | Osorio et al. | 600/544 |
| 6,690,974 | B2 * | 2/2004 | Archer et al. | 607/45 |
| 7,174,213 | B2 * | 2/2007 | Pless | 607/45 |
| 7,263,467 | B2 * | 8/2007 | Sackellares et al. | 702/183 |
| 7,373,199 | B2 * | 5/2008 | Sackellares et al. | 600/544 |
| 2004/0122335 | A1 | 6/2004 | Sackellares et al. | |

OTHER PUBLICATIONS

General redundancy optimization method for cooperating manipulators using quadratic inequality constraints Woong Kwon; Beom Hee Lee; Systems, Man and Cybernitcs, Part A, IEEE Transactions on vol. 29, Issue 1, Jan. 1999 pp. 41-51 Digital Object Identifier 10.1109/3468.736359.*

(Continued)

*Primary Examiner*—Michael B Holmes
(74) *Attorney, Agent, or Firm*—Alston & Bird LLP

(57) ABSTRACT

An exemplary method for analyzing behavior of a system includes receiving dynamical measurement data regarding the system, applying a quadratically constrained quadratic 0-1 problem to identify data among the received data, and storing the identified data. An exemplary seizure warning method includes continuously calculating $STL_{max}$ values, identifying critical sites by applying a quadratically constrained quadratic 0-1 solution to data (e.g. $STL_{max}$ profiles) derived from pre-seizure onset and post-seizure onset EEG signals, monitoring a T-index curve of the identified critical sites, warning of an impending seizure, observing a seizure and then repeating the cycle by identifying critical sites using the new data, and then monitoring them.

18 Claims, 7 Drawing Sheets

OTHER PUBLICATIONS

Quadratically constrained attitude control via semidefinite programming Yoonsoo Kim; Mesbahi, M.; Automatic Control, IEEE Transactions on vol. 49, Issue 5, May 2004 pp. 731-735 Digital Object Identifier 10.1109/TAC.2004.825959.*

Redundancy optimization for cooperating manipulators using quadratic inequality constraints Kwon, W.; Lee, B.H.; Kwon, W.H.; Choi, M.H.; Lee, S.H.; Robotics and Automation, 1998. Proceedings. 1998 IEEE International Conference on vol. 2, May 16-20, 1998 pp. 1528-1533 vol. 2 Digital Object Idenfifier 10.1109/ROBOT.1998.677337.*

Formulation of Closed-Loop Min-Max MPC as a Quadratically Constrained Quadratic Program Diehl, M.; Automatic Control, IEEE Transactions on vol. 52, Issue 2, Feb. 2007 pp. 339-343 Digital Object Identifier 10.1109/TAC.2006.890372.*

Arabanel, H.D.I. (1996): Analysis of Observed Chaotic Data. Springer-Verlag, New York, 1996.

Athanasiou, G.G., Bachas, C.P., Wolf, W.F. (1987): Invariant Geometry of Spin-glass States. Phy. Rev. B 35, 1965-1968.

Babloyantz, A., Destexhe, A. (1986): Low dimensional chaos in an instance of epilepsy. Proc. Natl. Acad. Sci. USA 83, 3513-3517.

Barahona, F. (1982): On the computational complexity of spin glass models. J. Phys. A: Math. Gen. 15, 3241-3253.

Barahona, F. (1982): On the exact ground states of three-dimensional ising spin glasses. J. Phys. A: Math. Gen. 15: L611-L615.

Barlow, J.S. (1985): Methods of analysis of nonstationary EEGs with emphasis on segmentation techniques. J. Clin. Neutophysiol 2, 267-304.

Casdagli, M.C., Iasemidis, L.D., Sackellares, J.C., Roper, S.N., Gilmore, R.L., Savit, R.S. (1996): Characterizing nonlinearity in invasive EEG recordings from temporal lobe epilepsy. Physica D 99, 381-399.

Casdagli, M.C., Iasemidis, L.D., Roper, S.N., Gilmore, R.L., Savit, R.S., Sackellares, J,C. (1997): Nonlinearity in invasive EEG recordings from patients with temporal lobe epilepsy. Electroenceph. Clin. Neurophysiol. 102, 98-105.

Shiau, D.S., Luo, Q., Gilmore, S.L., Roper, S.N., Pardalos, P.M., Sackellares, J.C., Iasemidis, L.D. (2000): Epileptic seizures resetting revisited. Epilepsia. 41, S7, 208-209.

Elger, C.E., Lehnertz, K. (1998): Seizure prediction by non-linear time series analysis of brain electrical activity. Europ. J. Neurosci. 10, 786-789.

Feber, F. (1987): Treatment of some nonstationarities in the EEG. Neuropsychobiology 17, 100-104.

Frank, W.G., Lookman, T., Nerenberg, M.A., Essex, C., Lemieux, J., Blume, W. (1990): Chaotic time series analyses of epileptic seizures. Physica D 46, 427-438.

Janse, B.H., Cheng, W.K. (1988): Structural EEG analysis. Int. J. Biomed. Comput. 23, 221-237.

Horst, H., Pardalos, P.M., Thoai, V. (1995): Introduction to global optimization, Series on Nonconvex Optimization and its Applications. Kluwer Academic Publishers, Dordrecht.

Iasemidis, L.D., Zaveri, H.P., Sackellares, J.C., Williams, W.J. (1988): Phase space analsis of EEG in temporal lobe epilepsy. IEEE Eng. in Medicine and Biology Society, 10th Ann. Inst.. Conf., 1201-1203.

Iasemidis, L.D., Zaveri, H.P., Sackellares, J.C., Williams, W.J. (1988): Linear and nonlinear modeling of ECoG in temporal lobe epilepsy. 25th Annual Rocky Mountain Bioengineering Symposium 24, 187-193.

Iasemidis, L.D., Zaveri, H.P., Sackellares, J.C., Williams, W.J., Hood, T.W. (1988): Nonlinear dynamics of electrocorticographic data. J. of Clinical Neurophysiology 5, 339.

Iasemidis, L.D., Sackellares, J.C. (1990): Long time scale Temporospatial Patterns of entrainment in preictal ECoG data in human temporal lobe epilepsy. Epilepsia 31, 621.

Iasemidis, L.D., Sackellares, J.C., Zaveri, H.P., Williams, W.J. (1990): Phase space topography of the electrocorticograms and the Lyapunov exponent in partial seizures. Brain Topogr 2, 187-201.

Iasemidis, L.D. (1991): On the dynamics of the human brain in temporal lobe epilepsy. Ph.D. dissertation, University of Michigan, Ann Arbor.

Iasemidis, L.D., Sackellares, J.C. (1991): The evolution with time of the spatial distribution of the largest Lyapunov exponent on the human epileptic cortex. In: Duke, D.W., Pritchard, W.S., eds., Measuring Chaos in the Human Brain, 49-82. World Scientific, Singapore.

Iasemidis, L.D., Sackellares, J.C., Savit, R.S. (1993): Quantification of hidden time dependencies in the EEG within the framework of nonlinear dynamics. In: Jansen, B.H., Brandt, M.E., eds., Nonlinear dynamical analysis of the EEG, 30-47. World Scientific, Singapore.

Iasemidis, L.D., Savit, R.S., Sackellares, J.C. (1993): Time dependencies in partial epilepsy. Epilepsia vol. 34S, 130-131.

Iasemidis, L.D., Olson, L.D., Sackellares, J.C., Savit, R. (1994): Time dependencies in the occurences of epileptic seizures: a nonlinear approach. Epilepsy Research 17, 81-94.

Iasemidis, L.D., Barreto, A., Gilmore, R.L., Uthman, B.M., Roper, S.N., Sackellares, J.C. (1994): Spatio-temporal evolution of dynamical measures precedes onset of mesial temporal lobe seizures. Epilepsia 35S, 133.

Iasemidis, L.D., Sackellares, J.C. (1996): Chaos theory and epilepsy. The Neuroscientist 2, 118-126.

Iasemidis, L.D., Konstantinos E. Pappas, Principe, IC., Sackellares, J.C. (1996): Spatiotemporal dynamics of human epileptic seizures. In: Harrison, R.G., Weiping, L., Ditto, W., Pecora, L., Vohra, S. eds., 3rd Experimental Chaos Conference, 26-30. World Scientific, Singapore.

Iasemidis, L.D., Pappas, K.E., Gilmore, R.L., Roper, S.N., Sackellares, J.C. (1996): Detection of the preictal transition state in scalp-sphenoidal EEG recordings. Annual American Clinical Neurophysiology Society Meeting, Boston, Sep. 8-9.

Iasemidis, L.D., Pappas, K.E., Gilmore, R.L., Roper, S.N., Sackellares, J.C. (1996): Preictal entrainment of a critical cortical mass is a necessary condition for seizure occurence. Epilepsia 37S5, 90.

Iasemidis, L.D., Gilmore, R.L., Roper, S.N., Sackellares, J.C. (1997): Dynamical interaction of the epileptogenic focus with extrafocal sites in temporal lobe epilepsy (TLE); Ann. Neurol., vol. 42, pp. 429.

Iasemidis, L.D., Principe, J.C., Czaplewski, J.M., Gilmore, R.L., Roper, S.N., Sackellares, J.C. (1997): Spatiotemporal transition to epileptic seizures: a nonlinear dynamical analysis of scalp and intracranial EEG recordings. In: Silva, F.L., Principe, J.C., Almeida, L.B., eds., Spatiotemporal Models in Biological and Artificial Systems, 81-88. IOS Press, Amsterdam.

Iasemidis, L.D., Sackellares, J.C., Gilmore, R.L., Roper, S.N. (1998): Automated seizure prediction paradigm. Epilepsia, vol. 39, pp. 56.

Iasemidis, L.D., Shiau, D-S., Sackellares, J.C., Pardalos, P.M. (1999): Transition to epileptic seizures: Optimization. In: Du DZ, Pardalos PM and Wang J, eds. DIMACS series in Discrete Mathematics and Theoretical Computer Science. American Mathematical Society, Providence, 55-74.

Iasemidis, L.D., Principe, J.C., Sackellares, J.C. (2000): Measurement and quantification of spatiotemporal dynamics of human epileptic seizures. In: Akay, M., ed., Nonlinear signal processing in medicine. IEEE Press, vol. II, pp. 1-27.

Iasemidis, L.D., Pardalos, P.M., Sackellares, J.C., Shiau, D-S. (2001): Quadratic binary programming and dynamical system approach to determine the predictability of epileptic seizures. J. Combinatorial Optimization 5, 9-26.

Iasemidis, L. D., Shiau, D.-S., Pardalos, P.M., Sackellares, J.C. (2001): Phase Entrainment and Predictability of Epileptic Seizures. In: Pardalos, P.M., Principe, J.C., eds., Biocomputing. Kluwer Academic Publishers, Dordrecht, pp. 1-22.

Iasemidis, L.D., Shiau, D-S., Sackellares, J.C , Pardalos, P.M., Prasad, A. (2002): Dynamical resetting of the human brain at epileptic seizures: application of nonlinear dynamics and global optimization techniques. IEEE Transactions on Biomedical Engineering, submitted.

Lehnertz, K., Elger, C.E. (1998): Can epileptic seizures be predicted? Evidence from nonlinear time series analysis of brain electrical activity. Phys. Rev. Lett. 80, vol. 22, 5019-5022.

Litt, B., Esteller, R., Echauz, J., Maryann, D.A., Shor, R., Henry, T., Pennell, P., Epstein, C., Bakay, R., Dichter, M., Vachtsevanos, G. (2001): Epileptic seizures may begin hours in advance of clinical onset: A report of five patients. Neuron 30, 51-64.

Martinerie, J., Van Adam, C., Le Van Quyen, M. (1998): Epileptic seizures can be anticipated by non-linear analysis. Nature Medicine 4, 1173-1176.

Mezard, M., Parisi, G., Virasoro, M. A. (1987): Spin Glass Theory and Beyond. World Scientific, Singapore.

Olson, L.D., Iasemidis, L.D., Sackellares, J.C. (1989): Evidence that interseizure intervals exhibit low dimensional dynamics. Epilepsia 30, 644.

Packard, N.H., Crutchfield, J.P., Farmer, J.D., Shaw R.S. (1980): Geometry from a time series. Phys. Rev. Lett. vol. 45, No. 9, 712-716.

Palus, M., Albrecht, V., Dvorak, I. (1993): Information theoretic test for nonlinearlity in time series. Phys. Rev. A 175, 203-209.

Pardalos, P.M., Rodgers, G. (1989): Parallel branch and bound algorithms for quadratic zero-one programs on the Hypercube Architecture., Annals. Of Operations Research, 22, pp. 271-292.

Pardalos, P.M., Rodgers, G. (1990): Computational aspects of a branch and bound algorithm for quadratic zero-one programming. Computing 45, 131-144.

Rapp, P.E., Zimmerman, I.D., Albano, A.M. (1986): Experimental studies of chaotic neural behavior: cellular activity and electroencephalographic signals. In: Othmer HG, ed. Nonlinear Oscillations in Biology and Chemistry, 175-805. Springer-Verlag, Berlin.

Sackellares, J.C., Iasemidis, L.D., Pappas, K.E., Gilomre, R.L., Uthman, B.M., Roper, S.N. (1995): Dynamical studies of human hippocampus in limbic epilepsy. Neurology, vol. 45, Supp. 4, p. A404.

Sackellares, J.C., Iasemidis, L.D., Gilmore, R.L., Ropper, S.N. (1997): Epileptic seizures as neural resetting mechanisms. Epilepsia 38, S3, 189.

Sackellares, J.C., Iasemidis, L.D., Shiau, D-S. (1999): Detection of the preictal transition in scalp EEG. Epilepsia 40, 176.

Sackellares, J.C. Iasemidis, L.D., Shiau, D-S, Gilmore, R.L., Roper, S,N. (2002): Epilepsy—when chaos fails. In: Lehnertz K, Arnhold J, Grassberger P and Elger CE, eds. Chaos in the brain? World Scientific, Singapore., pp. 112-133.

Sackellares, J.C., Iasemidis, L.D., Pardalos, P.M., Shiau, D.-S. (2001): Combined Application of Global Optimization and Nonlinear Dynamics to Detect State Resetting in Human Epilepsy. In: Pardalos, P.M., Principe, J.C., eds., Biocomputing. Kluwer Academic Publishers, Dordrecht, pp. 1-9.

Takens, F. (1981): Detecting strange attractors in turbulence. In: Rand, D.A. and Young, L.S., eds. Dynamical systems and turbulence, Lecture notes in mathematics. Springer-Verlag, Heidelburg.

Theiler, J. (1986): Spurious dimension from correlation algorithms applied to limited time-series data. Phys. Rev. A 34, 2427-2432.

Theiler, J., Rapp, P.E. (1996): Re-examination of the evidence for low-dimensional, nonlinear structure in the human electroencephalogram. Electroencephalography Clin. Neurophysiol. 98, 213-222.

Wolf, A., Swift, J.B., Swinney, H.L., Vastano, J.A. (1985): Determining Lyapunov exponents from a time series. Physica 16D, 285-317.

Wolf, A., Vastano, J.A. (1986): Intermediate length scale effects in Lyapunov exponent estimation. In: Mayer-Kress, G. ed. Dimensions and Entropies in Chaotic Systems: Quantification of Complex Behavior. Springer-Verlag, Berlin 94-99.

* cited by examiner

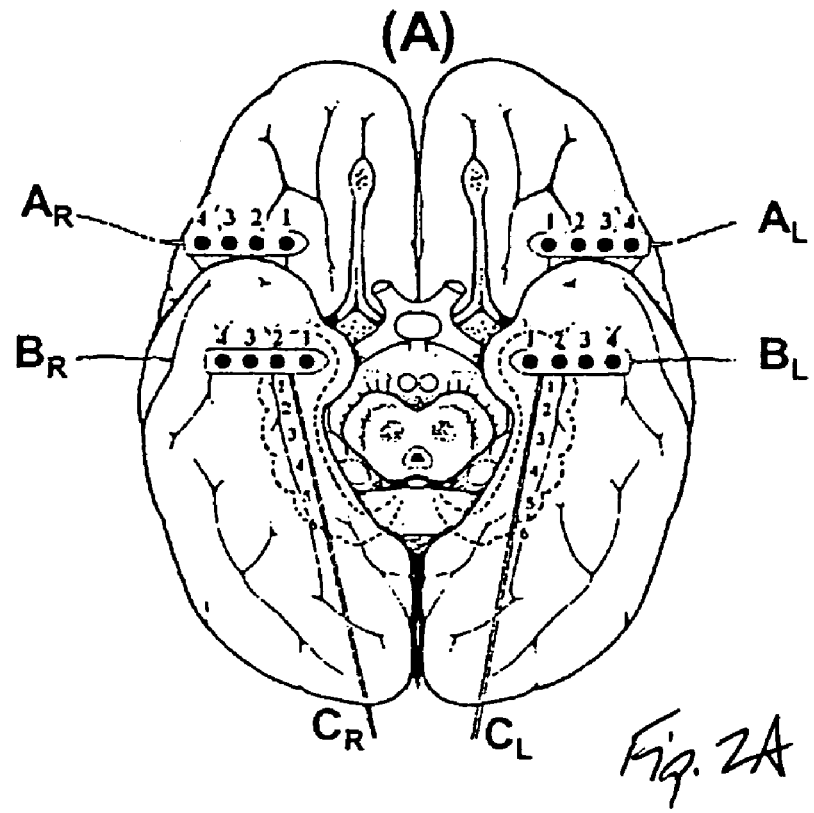
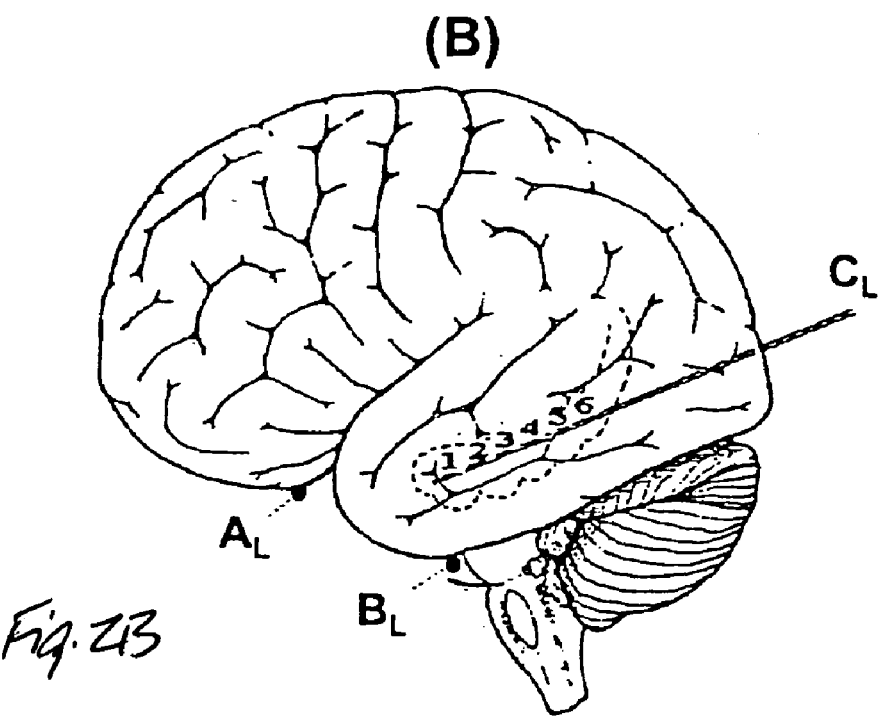

OPTIMIZATION OF SPATIO-TEMPORAL PATTERN PROCESSING FOR SEIZURE WARNING AND PREDICTION

PRIORITY CLAIM

This application claims priority under 35 U.S.C. § 119(e) to U.S. Provisional Application No. 60/495,702 filed in the U.S. Patent and Trademark Office on 18 Aug. 2003. U.S. Provisional Application No. 60/495,702 is hereby incorporated by reference.

STATEMENT REGARDING FEDERALLY SPONSORED RESEARCH AND DEVELOPMENT

The research and development effort associated with the subject matter of this patent application was supported by the National Institutes of Health (NIH) under grant no. R01 EB002089.

RELATED APPLICATIONS

This application is related to U.S. Pat. No. 6,304,775, U.S. patent application Ser. No. 10/648,354 and U.S. application Ser. No. 10/673,329, now U.S. Pat. No. 7,263,467, all of which are hereby incorporated by reference.

BACKGROUND INFORMATION

A multidimensional system is a system that exhibits behavior autonomously or as a function of multiple variables in response to a system input. A chaotic system is one that exhibits chaotic behavior (i.e., behavior characterized by random responses) during normal operation. The brain is an example of a multidimensional system that also exhibits chaotic behavior during normal operation. In a relatively significant percentage of the human population, the brain experiences periodic, abnormal episodes characterized by non-chaotic behavior. This abnormal behavior may be caused by a wide variety of conditions. Epilepsy is one of these conditions.

Epilepsy is a chronic disorder characterized by recurrent brain dysfunction caused by paroxysmal electrical discharges in the cerebral cortex. At any given time, Epilepsy affects approximately 50 million people worldwide. If untreated, an individual afflicted with epilepsy is likely to experience repeated seizures, which typically involve some level of impaired consciousness. Some forms of epilepsy can be successfully treated through medical therapy. However, medical therapy is less effective with other forms of epilepsy, including Temporal Lobe Epilepsy (TLE) and Frontal Lobe Epilepsy (FLE). With TLE and FLE, removing the portion of the hippocampus and/or cerebral cortex responsible for initiating the paroxysmal electrical discharges, known as the epileptogenic focus, is sometimes performed in an effort to control the seizures.

For quite some time, the medical community has attempted to develop techniques that provide seizure prediction and/or seizure warning, where seizure prediction will be understood to involve a long-range forecast of seizure-onset time, and seizure warning will be understood to involve a long-range indication of conditions conducive to an impending seizure. Any such technique would certainly have numerous clinical and non-clinical application. For example, in order to more effectively treat certain Epilepsy patients, such a technique might be used in conjunction with a device, perhaps an implanted device, designed to deliver a dosage of anti-seizure medication into the patient's bloodstream for the purpose of averting an impending seizure.

In another example, such a technique could be used during pre-surgical evaluations to assist in pinpointing the epileptogenic focus, which is to be removed during surgery. It is understood that during a seizure, blood flow to the epileptogenic focus significantly increases. If certain radio-labeled ligands are injected into the patient's bloodstream in a timely manner, it is possible to monitor that increased blood flow using radiography, thereby allowing a physician to accurately pinpoint the boundaries of the epileptogenic focus. A true seizure prediction and/or warning technique would provide an indication of an impending seizure well in advance and provide sufficient time to prepare for and administer, for example, the aforementioned radiography ligand.

One of the most important tools for evaluating the physiological state of the brain is the electroencephalogram (EEG). The standard for analyzing and interpreting an EEG is visual inspection of the graphic tracing of the EEG by a trained clinical electroencephalographer. However, there is no established method for predicting seizure onset or for providing a seizure warning well before seizure onset by visually analyzing an EEG. Moreover, the use of traditional signal processing techniques on EEG signals has likewise yielded little practical information. These traditional techniques are limited in their effectiveness because the brain is a multidimensional system that produces nonlinear signals with spatial as well as temporal properties. Thus, traditional signal processing techniques employing standard, linear, time series analysis methods cannot detect the spatio-temporal properties that are critical in providing effective seizure warning and prediction.

Commonly assigned U.S. Pat. No. 6,304,775, however, describes systems and methods capable of effectively generating true seizure warnings and predictions well in advance of impending seizures. The systems and methods described in this patent take advantage of the spatio-temporal characteristics exhibited by certain sites within the brain, when compared with the spatio-temporal characteristics exhibited by other sites within the brain, as these characteristics are noticeably different prior to an impending seizure as compared to the spatio-temporal characteristics exhibited by these same sites during seizure free intervals. In fact, these spatio-temporal characteristics may be noticeable hours, and in some cases, days before the occurrence of a seizure. As such, the systems and methods described in U.S. Pat. No. 6,304,775 use these differences as a seizure transition indicator.

U.S. Pat. No. 6,304,775 specifically describes, among other things, a technique that provides timely impending seizure warning (ISW), seizure susceptibility period detection (SSPD) and time to impending seizure prediction (TISP). The technique involves acquiring electrical or electromagnetic signals generated by the brain, where each signal corresponds to a single EEG electrode or channel. Each signal is pre-processed (e.g., amplified, filtered, digitized) and sampled. This results in a sequence of digital samples for each signal over a period of time, referred to therein as an epoch. The samples are then used to generate a phase space portrait for each signal epoch.

For each phase space portrait, a parameter reflecting rate of divergence is computed based on adjacent trajectories in the phase space, where rate of divergence, in turn, reflects the chaoticity level of the corresponding signal. In U.S. Pat. No. 6,304,775, the parameter that is used for this purpose is the short-term, largest Lyapunov exponent ($STL_{max}$).

In general, the $STL_{max}$ values associated with each EEG signal (i.e., each EEG channel) are compared to the $STL_{max}$ values associated with each of the other channels. In U.S. Pat. No. 6,304,775, the comparisons are preferably achieved by applying a T-statistic, which results in a sequence of statistical values, or T-index values, for each channel pair, where a sequence of T-index values represents a level of correlation or entrainment between the spatio-temporal response associated with the two channels that make up each channel pair.

The technique, when first employed, goes through an initialization period. During this initialization period, a number of "critical" channel pairs is identified, where a critical channel pair is defined in U.S. Pat. No. 6,304,775 as a pair of channels that exhibits a relatively high level of entrainment (i.e., relatively low T-index values for a predefined period of time) prior to seizure onset.

During the initialization period, a patient may experience one or more seizures. After each, the list of critical channel pairs is updated. Eventually, the list of critical channel pairs is considered sufficiently refined, and the initialization period is terminated. Thereafter, the ISW, SSPD and TISP functions may be activated and the T-index values associated with the critical channel pairs are monitored and employed in generating timely ISWs, SSPDs and/or TISPs.

SUMMARY

Epileptic seizures can be predicted based on spatiotemporal dynamics in electroencephalograms (EEGs) from patients with temporal lobe epilepsy. There is a temporal transition before seizure, characterized by progressive convergence (entrainment) of dynamical measures such as maximum Lyapunov exponents ($STL_{max}$) at specific anatomical areas in the neocortex and hippocampus of the brain. These sites of epileptogenic focus are also termed "critical sites". If it is known which sites will participate in the next preictal transition, then the next transition can be detected in time to warn of an impending epileptic seizure. Different sets of cortical sites may exhibit preictal transition from one seizure to the next. Also, entrainment of critical sites is reset after each seizure—that is, the $STL_{max}$ profiles diverge after seizures. Complete or partial postictal resetting of preictal entrainment appears to affect the route to subsequent seizures. Accordingly, ensuring that an optimal group of critical sites shows this divergence of STLmax profiles can enhance the prediction of subsequent seizures.

In accordance with exemplary methods, ensuring that an optimal group of critical sites shows this postictal divergence of $STL_{max}$ profiles is performed by reformulating the optimization problem to add one more quadratic constraint, and thus end up with a quadratically constrained quadratic 0-1 problem. In other words, in exemplary methods quadratic 0-1 programming is used to identify critical sites to be monitored for preictal transitions. In a first exemplary method, quadratic 0-1 programming is linearized, and one more linearized constraint is added prior to solving the problem to identify critical sites. In a second exemplary method, a linear mixed integer 0-1 problem that applies Karush-Kuhn Tucker conditions is modified by adding a first-order derivative of the quadratic constraint before being solved.

An exemplary seizure warning method includes continuously calculating $STL_{max}$ values, identifying critical sites by applying a quadratically constrained quadratic 0-1 solution to data (e.g. $STL_{max}$ profiles) derived from pre-seizure onset and post-seizure onset EEG signals, monitoring a T-index curve of the identified critical sites, warning of an impending seizure, observing a seizure and then repeating the cycle by identifying critical sites using the new data, and then monitoring them.

An exemplary method for analyzing behavior of a system includes receiving dynamical measurement data regarding the system, applying a quadratically constrained quadratic 0-1 problem to identify data among the received data, and storing the identified data.

BRIEF DESCRIPTION OF THE DRAWING FIGURES

FIG. 2B illustrates another exemplary method.

FIGS. 2A, 2B illustrate exemplary sites in a human brain that can be monitored in accordance with exemplary methods.

DETAILED DESCRIPTION

Figure 1A:
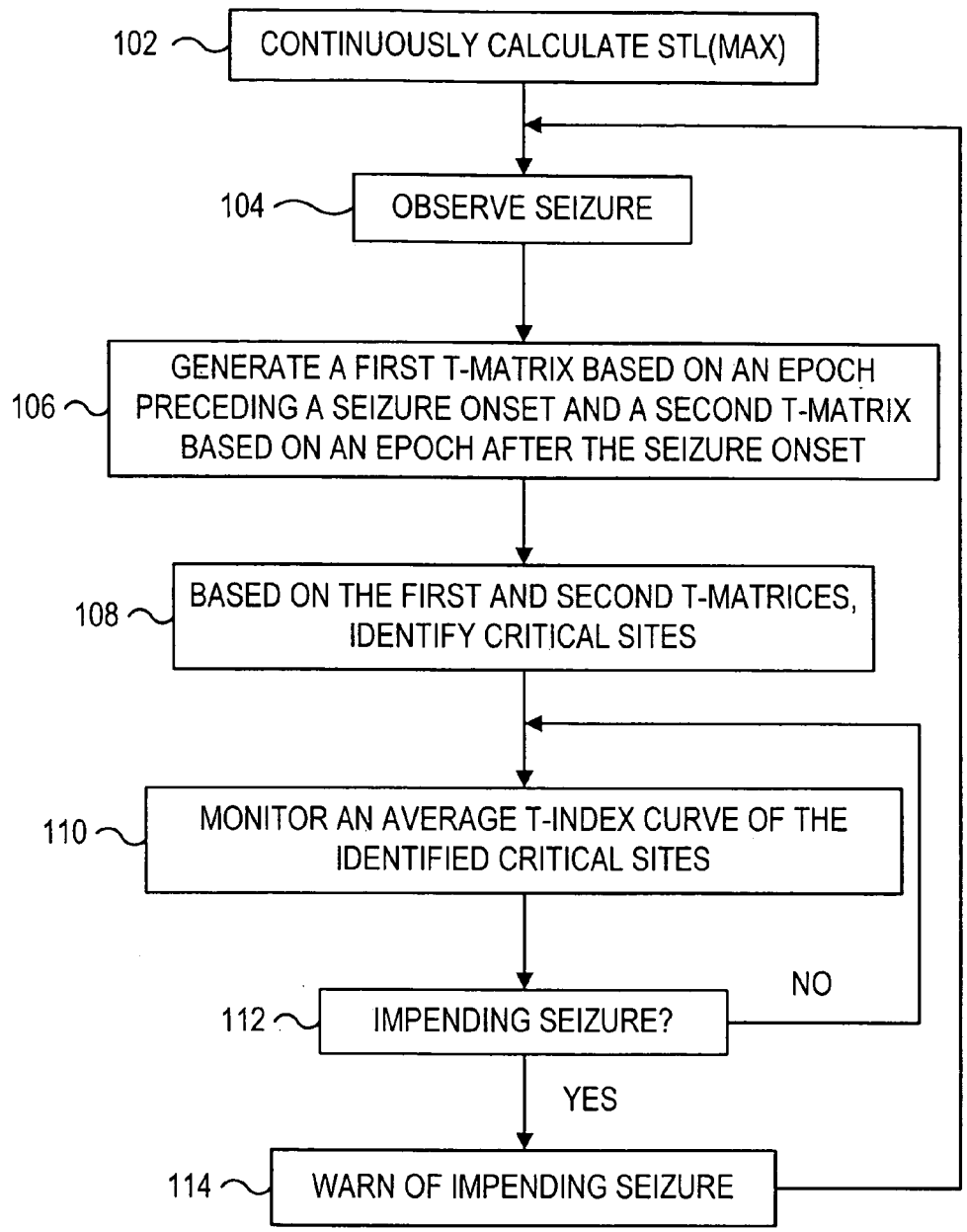
FIG. 1A illustrates an exemplary method.

FIG. 1A shows an exemplary method for predicting epileptic seizures, which can also be used to predict behavior or change in state of any complex system reflected in multi-dimensional time series information about the system. In a first step 102, a dynamical measure such as $STL_{max}$ is continuously calculated. In an exemplary method, this calculation is continuously or periodically performed while the other steps shown in FIG. 1 are performed. In a next step 104, a seizure is observed. In a next step 106, one or more measures of statistical difference between the dynamical measures are generated, for example first T-matrix can be generated based on an epoch preceding a seizure onset, and a second T-matrix can be generated based on an epoch after the seizure onset. In a next step 108, critical sites are identified based on the measures of statistical difference, for example the first and second T-matrices. In particular, the measures of statistical difference can be supplied in a quadratically constrained quadratic 0-1 knapsack problem or model of the system being analyzed, which can be solved to minimize the measures of statistical difference between values of the dynamical measures (or mean values of the dynamical measures) to identify system sites or elements/components that are behaving in a similar manner, for example critical cortical sites of the brain being monitored with regard to epileptic seizure. In a next step 110, an average t-index curve of the identified critical sites is monitored. In a next step 112, a determination is made based on the monitoring of step 110, whether a seizure is impending. If the determination is no, then control returns to step 108. If the determination is yes, then control proceeds to step 114, where a warning is made that a seizure is impending. From step 114, control returns to step 104.

Figure 1B:
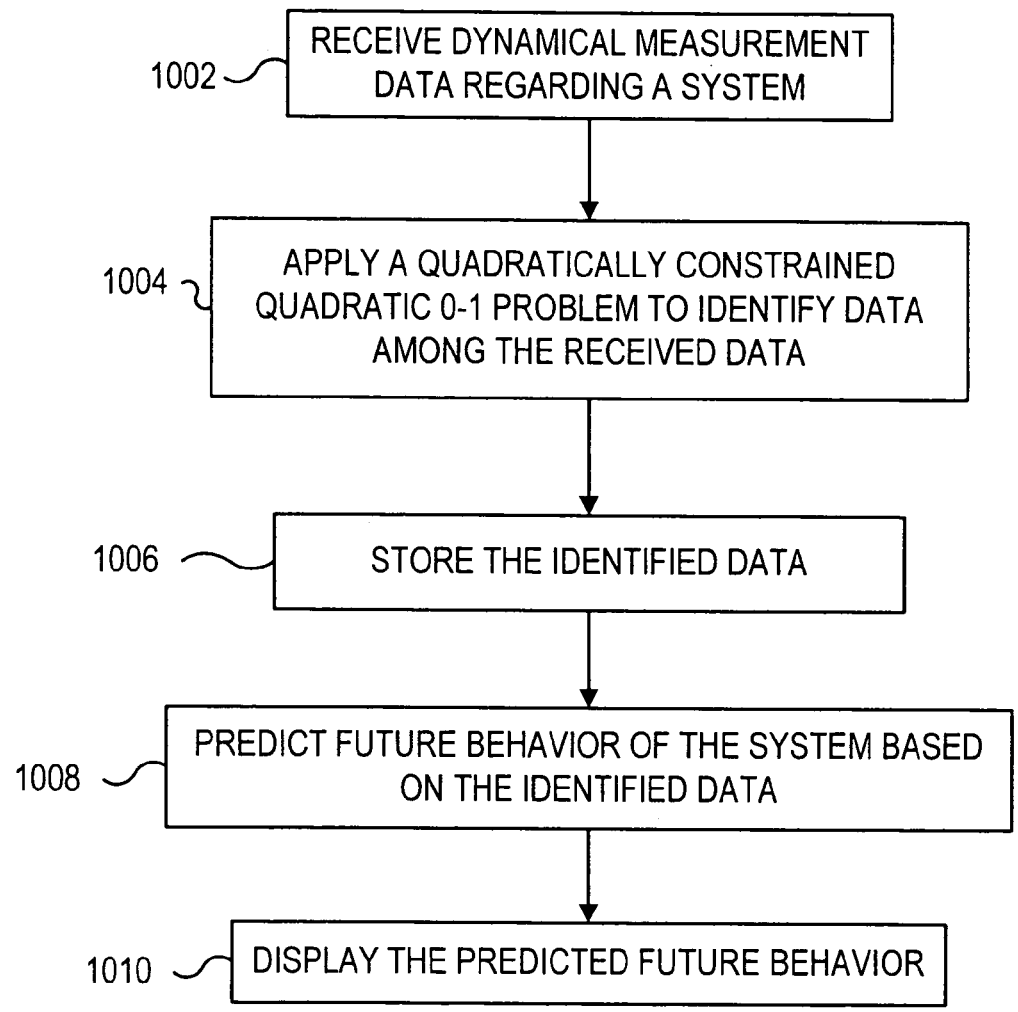

FIG. 1B shows another, generally applicable exemplary method for predicting behavior or change in state of any complex system, where for example the status or performance of the system is reflected in multi-dimensional time series information about the system. The method is especially suitable for implementation on a computer or computer system. In a first step 1002, dynamical measurement data regarding the system is received. This data can include, for example, one or more of raw data, maximum Lyapunov exponents, angular frequency, entropy, mutual information, and so forth.

From step 1002 control proceeds to step 1004, where a quadratically-constrained, quadratic 0-1 problem is applied to the received data using techniques described herein to identify critical data components among the received data, for example to identify critical sites or sources of data that indicate or correlate with behavior (including future behavior) of the system. For example, the problem can be solved by linearizing the quadratic objective function by introducing a new variable for each product of two variables and adding some additional constraints, and then formulating and solving the problem as a linear 0-1 problem. In another example, the problem is solved by applying Karush-Kuhn Tucker optimality conditions and formulating the problem with conditions as a linear mixed integer 0-1 problem.

From step 1004 control proceeds to step 1006, where the identified data is stored, for example in long term and/or short term memory of a computer, and/or in one or more data storage devices such as a hard disc drive, floppy disc drive, and so forth. From step 1006, control proceeds to step 1008, where future behavior of the system is predicted based on the identified data. The prediction can be performed using known techniques, given an optimized selection of data and/or data sources provided in step 1004. From step 1008 control proceeds to step 1010, where the predicted future behavior is displayed. The predicted future behavior can also be stored.

The background and details of the method illustrated in FIG. 1A, and which also apply to FIG. 1B, will now be explained. Since the brain is a nonstationary system, algorithms used to estimate measures of the brain dynamics should be capable of automatically identifying and appropriately weighing existing transients in the data. In a chaotic system, orbits originating from similar initial conditions (nearby points in space) diverge exponentially (an expansion process). The rate of divergence can be an important aspect of the system dynamics and can be reflected in the value of Lyapunov exponents.

Methods for estimating $STL_{max}$ are described in detail elsewhere, and thus only a short description will follow. Construction of the embedding phase space from a data segment x(t) of duration T is made with the method of delays. The vectors $X_i$ in the phase space are constructed as:

$$X_i = (x(t_i), x(t_i+\tau) \ldots x(t_i+(p-1)*\tau)) \quad (1)$$

where $\tau$ is the selected time lag between the components of each vector in the phase space, p is the selected dimension of the embedding phase space, and $t_i \in [1, T-(p-1)\tau]$. If we denote by L the estimate of the short term largest Lyapunov exponent $STL_{max}$ then:

$$L = \frac{1}{N_a \Delta t} \sum_{i=1}^{N_a} \log_2 \frac{|\delta X_{i,j}(\Delta t)|}{|\delta X_{i,j}(0)|} \quad (2)$$

with $$\delta X_{i,j}(0) = X(t_i) - X(t_j) \quad (3)$$

$$\delta X_{i,j}(\Delta t) = X(t_i + \Delta t) - X(t_j + \Delta t) \quad (4)$$

where $X(t_i)$ is the point of the fiducial trajectory $\phi_t(X(t_0))$ with $t = t_i$, $X(t_0) = (x(t_0), \ldots, x(t_0+(p-1)*\tau))$, and $X(t_j)$ is a properly chosen vector adjacent to $X(t_i)$ in the phase space;

$\delta X_{i,j}(0) = X(t_i) - X(t_j)$ is the displacement vector at $t_i$, that is a perturbation of the fiducial orbit at $t_i$, and $\delta X_{i,j}(\Delta t) = X(t_i + \Delta t) - X(t_j + \Delta t)$ is the evolution of this perturbation after time $\Delta t$;

$t_i = t_0 + (i-1) * \Delta t$ and $t_j = t_0 + (j-1) * \Delta t$, where $i \in [1, N_a]$ and $j \in [1, N]$ with $j \neq i$;

$\Delta t$ is the evolution time for $\delta X_{i,j}$, that is, the time one allows $\delta X_{i,j}$ to evolve in the phase space—if the evolution time $\Delta t$ is given in seconds, then L is in bits per second;

$t_0$ is the initial time point of the fiducial trajectory and coincides with the time point of the first data in the data segment of analysis—in the estimation of L, for a complete scan of the attractor, $t_0$ should move within $[0, \Delta t]$; and $N_a$ is the number of local $L_{max}$'s that will be estimated within a duration T data segment—therefore, if $D_t$ is the sampling period of the time domain data, $T=(N-1)D_t=N_a\Delta t+(p-1)\tau$.

The short term largest Lyapunov exponent $STL_{max}$ can be computed using the method proposed by L. D. Iasemedis, Ph.D. dissertation University of Michigan, Ann Arbor, 1991, entitled On the dynamics of the human brain in temporal lobe epilepsy, which is a modification of the method described in Wolf, et al.'s Determining Lyapunov exponents from a time series, Physica D vol. 16, pp. 285-317, 1985. The measure is called "short term" to distinguish it from those used to study autonomous dynamical systems studies. Modification of Wolf's algorithm is necessary to better estimate $STL_{max}$ in small data segments that include transients, such as interictal spikes. The modification is primarily in the searching procedure for a replacement vector at each point of a fiducial trajectory. For example, the crucial parameter of the $L_{max}$ estimation procedure to distinguish between the preictal, ictal and postictal stages was not the evolution time $\Delta t$ nor the angular separation $V_{i,j}$ between the evolved displacement vector $\delta X_{i-1,j}(\Delta t)$ and the candidate displacement vector $\delta X_{i,j}(0)$. Instead, the crucial parameter is the adaptive estimation in time and phase space of the magnitude bounds of the candidate displacement vector to avoid catastrophic replacements.

Having estimated the $STL_{max}$ temporal profiles at individual cortical sites, and as the brain proceeds towards the ictal state, the temporal evolution of the stability of each cortical site is quantified. However, the system under consideration (the brain) has a spatial extent and, as such, information about the transition of the system towards the ictal state can also be included in the interactions of its spatial components. The spatial dynamics of this transition are captured by consideration of the relations of the $STL_{max}$ between different cortical sites. For example, if a similar transition occurs at different cortical sites, the $STL_{max}$ of the involved sites are expected to converge to similar values prior to the transition. Such sites are termed "critical sites", and such a convergence is termed "entrainment". More specifically, in order for the dynamical entrainment to have a statistical content, a period is allowed over which the difference of the means of the $STL_{max}$ values is estimated. For example, a period of 10 minutes with moving windows including approximately 60 $STL_{max}$ values over time at each electrode site, can be used to test the dynamical entrainment at the 0.01 statistical significance level. The T-index can be employed (from the well-known paired T-statistics for comparison of means) as a measure of distance between the mean values of pairs of $STL_{max}$ profiles over time. The T-index at time t between electrode sites i and j is defined as:

$$T_{i,j}(t) = \frac{\sqrt{N} \times |E\{STL_{max,i} - STL_{max,j}\}|}{\sigma_{i,j}(t)} \quad (5)$$

where

E{.} is the sample average difference for the $STL_{max,i} - STL_{max,j}$ estimated over a moving window $w_t\lambda$ defined as:

$$w_t(\lambda) = \begin{bmatrix} 1 & \text{if } \lambda \in [t-N-1, t] \\ 0 & \text{if } \lambda \notin [t-N-1, t] \end{bmatrix}$$

where N is the length of the moving window. Then, $\sigma_{i,j}(t)$ is the sample standard deviation of the $STL_{max}$ differences between the electrode sites i and j within the moving window $w_t\lambda$. The thus defined T-index follows a t-distribution with N−1 degrees of freedom. For the estimation of the $T_{i,j}(t)$ indices, for example N=60 can be used (i.e., an average of 60 differences of $STL_{max}$ exponents between sites i and j per moving window of approximately 10 minutes duration). Therefore, a two-sided t-test with N−1(=59) degrees of freedom, at a statistical significance level α can be used to test the null hypothesis, $H_0$: "brain sites i and j acquire identical $STL_{max}$ values at time t". For example, α can be set to 0.01, the probability of a type I error, or better, the probability of falsely rejecting $H_0$ if $H_0$ is true is 1%. For the T-index to pass this test, the $T_{i,j}(t)$ value should be within the interval [0, 2.662].

As indicated above, in exemplary methods quadratic 0-1 programming is used to select critical cortical sites. The problem can be formulated as a quadratic 0-1 knapsack problem, with an objective function to minimize the average T-index (a measure of statistical distance between the mean values of $STL_{max}$) among electrode sites and the knapsack constraint to identify the number of critical cortical sites.

Let A be an n×n matrix, whose each element $a_{i,j}$ represents the T-index between electrode i and j. Define $x=(x_1, \ldots x_n)$ where each $x_i$ represents the cortical electrode site i. If the cortical site is selected to be one of the critical electrode sites, then $x_i=1$; otherwise, $x_i=0$.

In linearly constrained quadratic 0-1 programming, a quadratic function is defined on $R^n$ by $$\min f(x) = x^T AX, \; s.t. x_i \in \{0,1\}, \; i=1, \ldots, n \quad (6)$$

where A is an n×n matrix. Throughout this section the following notations will be used:

$\{0,1\}^n$: set of n dimensional 0-1 vectors.

$R^{n \times n}$: set of n×n dimensional real matrices.

$R^n$: set of n dimensional real vectors.

Next, we add a linear constraint, $$\sum_{i=1}^{n} x_i = k$$

to specify the number of critical electrode sites, k. We now consider the following linearly constrained quadratic problem:

$$P' : \min f(x) = x^T Ax, \; s.t. \sum_{i=1}^{n} x_i = k \text{ for some } k, x \in \{0,1\}^n, A \in R^{n \times n} \quad (7)$$

Problem P' can be formulated as a quadratic 0-1 problem of the form as in (8) below by using an exact penalty. If $A=(a_{i,j})$ then let $$M = 2\left(\sum_{j=1}^{n} \sum_{i=1}^{n} |a_{ij}|\right) + 1.$$

Then, we have the following equivalent problem P as follows:

$$P : \min g(x) = x^T Ax + M\left(\sum_{i=1}^{n} x_i - k\right)^2, \; s.t. x \in \{0,1\}^n, A \in R^{n \times n} \quad (8)$$

To solve this problem, in a first approach the quadratic objective function is linearized by introducing a new variable for each product of two variables and adding some additional constraints, and then formulating the problem as a linear 0-1 problem. In a second approach, the Karush-Khun Tucker optimality conditions are applied and then the conditions are formulated as a linear mixed integer 0-1 problem.

In the first approach, for each product $x_i x_j$, a new 0-1 variable is introduced, $x_{ij}=x_i x_j$ ($i \neq j$). Note that $x_{ii}=x_i^2=x_i$ for $x_i \in \{0,1\}$. After linearization, the equivalent linear 0-1 problem is given by:

$$\min \sum_{i} \sum_{j} a_{ij} x_{ij} \quad (9)$$

$$s.t. \sum_{i=1}^{n} x_i = k \quad (10)$$

$$x_{ij} \leq x_i, \text{ for } i,j=1, \ldots, n (i \neq j) \quad (11)$$

$$x_{ij} \leq x_j, \text{ for } i,j=1, \ldots, n (i \neq j) \quad (12)$$

$$x_i + x_j - 1 \leq x_{ij}, \text{ for } i, j=1, \ldots, n (i \neq j) \quad (13)$$

where $x_i \in \{0,1\}$ and $x_{ij} \in \{0,1\}$, i,j=1, \ldots, n.

The number of 0-1 variables has increased to $O(n^2)$.

In the second approach, consider the quadratic problem given by:

$$\min z(x) = x^T Ax, \; s.t. \sum_{i=1}^{n} x_i = k, x_i \geq 0, i=1, \ldots, n. \quad (14)$$

$$T_{i,j}(t) \frac{\sqrt{N} \times |E\{STL_{max,i} - STL_{max,j}\}|}{\sigma_{i,j}(t)}$$

and the T-index matrix has the same property as the Euclidean distance matrix, which is positive semidefinite; therefore, the T-index matrix is also positive semidefinite.

Corresponding to the above primal problem, we have a dual Lagrangian problem:

$$\max z(x) = -v^T A v + k^T s \quad (15)$$

$$s.t. -Av + s + y = 0, \text{ where } y \geq 0. \quad (16)$$

Taking v=x, we have the following Karush-Kuhn Tucker conditions:

$$\sum_{i=1}^{n} x_i = k, \text{ where } x \geq 0. \quad (17)$$

$$-Ax + s + y = 0, \text{ where } y \geq 0 \quad (18)$$

$$XYe = 0, \quad (19)$$

where X and Y are diagonal matrices having the coordinates of x and y as diagonal entries, respectively.

In the above KKT conditions, replace the last constraint with $y_i \leq \mu(1-x_i)$, for i=1, ..., n, where $\mu$ is an arbitrary large number, and then formulate the quadratic 0-1 problem as a linear mixed integer 0-1 problem given by:

$$\min \sum_{i=1}^{n} s_i \quad (20)$$

$$s.t. \sum_{i=1}^{n} x_i - k = 0 \quad (21)$$

$$-\sum_{j=1}^{n} a_{ij} x_j + s_i + y_i = 0, \text{ for } i = 1, \ldots, n \quad (22)$$

$$y_i - \mu(1-x_i) \leq 0, \text{ for } i=1, \ldots, n \quad (23)$$

where $x_i \in \{0,1\}$ and $s_i, y_i \leq 0$, for I=1, ..., n.

Applying CPLEX 7.0, this problem can be easily solved with n=30. In addition, this problem is computationally efficient as n increases because the number of 0-1 variables is O(n).

The brain resets after seizures, so that $STL_{max}$ profiles diverge after seizures. To ensure that the optimal group of critical sites shows this divergence, the optimization problem can be reformulated by adding one more quadratic constraint. The quadratically constrained quadratic 0-1 problem is given by:

$$\min x^T A x \quad (24)$$

$$s.t. \sum_{i=1}^{n} x_i = k \quad (25)$$

$$x^T B x \geq T_\alpha k(k-1) \quad (26)$$

where $x_i \in \{0,1\} \forall i \in \{1, \ldots, n\}$.

Note that the matrix $B=(b_{ij})$ is the T-index matrix of brain sites i and j within a time window (e.g., 10 minutes) after the onset of a seizure. $T_\alpha$ is the critical value of T-index, as previously defined, to reject $H_0$: "two brain sites acquire identical $STL_{max}$ values within time window $w_t(\lambda)$".

With one more quadratic constraint, the quadratic 0-1 problem becomes much harder to solve. Modifying the linear 0-1 problem of the first approach described above, this problem can be solved by adding one more linearized constraint. The equivalent linear 0-1 problem is given by:

$$\min \sum_i \sum_j a_{ij} x_{ij} \quad (27)$$

$$s.t. \sum_{i=1}^{n} x_i = k, \quad (28)$$

$$x_{ij} \leq x_i, \text{ for } i,j=1, \ldots, n (i \neq j) \quad (29)$$

$$x_{ij} \leq x_j, \text{ for } i,j=1, \ldots, n (i \neq j) \quad (30)$$

$$x_i + x_j - 1 \leq x_{ij}, \text{ for } i,j=1, \ldots, n (i \neq j) \quad (31)$$

$$\sum_i \sum_j b_{ij} x_{ij} \geq T_\alpha k(k-1) \quad (32)$$

where $x_i \in \{0,1\}$ and $x_{ij} \in \{0,1\}$, i, j=1, ..., n.

However, this formulation can be computationally inefficient as n increases. Accordingly, we modify the linear mixed integer 0-1 problem described above in the second approach (involving KKT), by adding the first-order derivative of the quadratic constraint and some additional constraints. The equivalent linear mixed integer 0-1 problem is given by:

$$\min \sum_{i=1}^{n} s_i \quad (33)$$

$$s.t. \sum_{i=1}^{n} x_i - k = 0 \quad (34)$$

$$-\sum_{j=1}^{n} a_{ij} x_j + s_i + y_i = 0, \text{ for } i = 1, \ldots, n \quad (35)$$

$$y_i - M(1-x_i) \leq 0, \text{ for } i=1 \ldots, n \quad (36)$$

$$h_i - M x_i \leq 0, \text{ for } i=1, \ldots, n \quad (37)$$

$$-\sum_{j=1}^{n} d_{ij} x_j + h_i \leq 0, \text{ for } i = 1, \ldots, n \quad (38)$$

$$\sum_{i=1}^{n} h_i \geq T_\alpha k(k-1) \quad (39)$$

where $x_i \in \{0,1\}$ and $s_i, y_i, h_i \geq 0$, for i, j=1, ... n.

Applying CPLEX 7.0, this problem can easily be solved with n=30. This formulation is very efficient and can be used to solve the quadratically constrained quadratic 0-1 problem iteratively.

As described herein, a) in the first approach a quadratic objective function is linearized by introducing a new variable for each product of two variables and adding some additional constraints, and then formulating the problem as a linear 0-1 problem, and b) in the second approach, the Karush-Khun Tucker optimality conditions are applied and then the conditions are formulated as a linear mixed integer 0-1 problem. In accordance with exemplary embodiments and methods, these first and second approaches can be applied to analyze behavior of any multidimensional system over time. For example, dynamical measures other than maximum Lyapunov exponents can be gathered and used, and other measures of distance or relationship between the dynamical measures besides T-indexes can be used when formulating the problem or modeling the system in question as a quadratically constrained quadratic 0-1 problem. The epileptic seizure example discussed herein involves entrainment of sites or elements of a complex system (the brain).

Exemplary embodiments and methods can also identify disentrainment or divergent or dissimilar behavior of sites or elements of a complex system being analyzed. Exemplary embodiments and methods can identify behavior of particular sites or elements of the complex system that correlates with or predicts a change in state of the complex system.

Thus, the exemplary methods described herein, in particular the first and second approaches for solving quadratically constrained quadratic 0-1 problems, can be applied to multidimensional time series data documenting behavior of a complex, multi-dimensional system to identify data and/or sources of the data that indicate or predict changes in a state of the system, for example online and/or in real time. For example, economic parameters can be analyzed quadratically constrained quadratic 0-1 programming to predict stock market behavior or changes such as a bull market or a stock market crash, changes in market conditions for a particular company or industry, and so forth.

As alternatives to Lyapunov exponents and T-indexes, other dynamical measures can be used, including for example: angular frequency; entropy; mutual information; and so forth. Measures most appropriate to the system being analyzed can be selected. For example, in a finance or economic application, use of correlation coefficient(s) may be most appropriate, and the constraints (e.g. conditions and characteristics) can be maximized accordingly, for example maximizing the correlation coefficient matrix when correlation coefficients form the dynamical measure. In general, many different measures can be used effectively when the exemplary approaches for solving quadratically constrained quadratic 0-1 problems described herein, are applied.

Other applications with respect to the human body are also possible. For example, with a vehicle or heavy equipment operator can be monitored for impending sleep or drowsiness beyond a certain threshold, a patient can be monitored for onset of systemic pain syndrome, migraine headaches, narcolepsy and so forth. State changes of varying rapidity and duration can be monitored and predicted, for example tremors, effects of Parkinsons disease, and so forth. Other areas of the brain besides those shown in FIGS. 2A, 2B can alternatively or additionally be monitored, for example deeper structures such as the thalamus and/or the basal ganglia, and any number of probes or sites can be used/monitored.

Exemplary methods and embodiments described herein encompass data derived from any source or method. For example, data regarding brain function can be obtained from any appropriate source, including electrical probes of varying size and number implanted directly in the brain, as well as non-invasive sources/techniques such as magnetoencephalograms, photon emission tomography (PET), single photon emission computed tomography (SPECT), and so forth, and brain activity can be detected based on blood flow to different areas of the brain, glucose metabolic rates within the brain, and so forth. Other data can also be used/correlated with brain performance data, for example activation of various muscles in the body (which can be measured in various ways including but not limited to monitoring local neural electrical signals, local chemical activity within/near the muscle, blood flow, tension of muscle tissue, motion or position of the limb or structure to which the muscle is attached, etc.) as well as positions or locations of body elements or extremities, behavior at brain-machine or body-machine (e.g. prosthetic) interfaces, and so forth. The data being considered or analyzed can also include stimulus to the system, for example intervening medical therapy that seeks to halt, reverse or restore a system state change (e.g. by electrically, chemically or magnetically affecting the brain), and thus exemplary methods and embodiments described.

In experiments performed by the inventors, datasets included continuous, long-term (3 to 12 days) multichannel intracranial EEG recordings that had been acquired from five patients with medically intractable temporal lobe epilepsy. The recordings were obtained as part of pre-surgical clinical evaluation. They were obtained using Nicolet BMSI 4000 and 5000 recording systems, using a 0.1 Hz high-pass and a 70 Hz low-pass filter. Each record included a total of 28 to 32 intracranial electrodes (8 subdural and 6 hippocampal depth electrodes for each cerebral hemisphere, as shown for example in FIGS. 2A, 2B respectively. Specifically, FIG. 2A shows an inferior transverse view of the brain, and FIG. 2B shows a lateral view of the brain. Subdural electrode strips were placed over the left orbitofrontal ($A_L$), right orbitofrontal ($A_R$), left subtemporal ($B_L$), and right subtemporal ($B_R$) cortex. Depth electrodes were placed in the left temporal depth ($C_L$) and right temporal depth ($C_R$) to record hippocampal activity. Characteristics of the recordings are outlined in Table 1 below.

TABLE 1

| Patient | Gender | Age | Number/ electrodes | Complex partial seizures | Partial, secondarily generalized seizures | Subclinical seizures | Total length of data (hours) | Range of seizure interarrival time |
| --- | --- | --- | --- | --- | --- | --- | --- | --- |
| 1 | F | 41 | 32 | 17 | 3 | 0 | 83.30 | 0.3-14.5 |
| 2 | M | 29 | 28 | 8 | 0 | 7 | 140.15 | 0.3-70.8 |
| 3 | F | 38 | 32 | 6 | 0 | 0 | 18.24 | 1.1-4.8 |
| 4 | M | 60 | 28 | 0 | 7 | 0 | 121.92 | 2.7-78.7 |
| 5 | F | 45 | 28 | 3 | 6 | 6 | 69.53 | 0.5-47.9 |

The recorded EEG signals were digitized, using a sampling rate of 200 Hz, and stored on magnetic media for subsequent off-line analysis. $STL_{max}$ values were iteratively calculated from sequential non-overlapping 10.24 second EEG epochs obtained from each electrode site, using methods described herein. The $STL_{max}$ method accomplishes a large data reduction (each 10.24 second EEG epoch becomes a single sample in the $STL_{max}$ profiles), and it is applied sequentially to each EEG channel, creating a new multichannel time series that is used for subsequent analysis.

Critical electrode sites were identified automatically by the optimization algorithm described herein, after the first seizure occurred. The critical sites were updated after each subsequent electrographic seizure. Selection of the critical electrode sites was accomplished in two steps, in a first step two T-matrices were generated, one from the 10-minute epoch prior to the seizure onset and the other from the 10-minute epoch after the seizure onset. This was accomplished by calculating the T-indices of $STL_{max}$ for all possible pairs of electrode sites. In the second step, the optimization algorithm described herein was applied on the two T-matrices as its objective functions to identify the most critical group of electrode sites. In this case, the algorithm basically identified the group of sites which were most entrained prior to the seizure, conditional on the disentrainment after the seizure onset. When selecting the critical sites, two parameters were trained in the algorithm: a number of sites (k) per group, and a number of groups (m) to be selected. For each patient, the first half of the seizures were used to train k(3~6) and m(1~5). The optimal parameter setting was then identified by observing the ROC curves of the seizure warning performance, and were later applied in the testing seizures.

Once groups of critical electrode sites were chosen, the average T-index value for each of the groups was continuously calculated from $STL_{max}$ profiles, using sequential 10-minute overlapping windows. The average T-index values were continuously compared to a preset threshold value ($T_\alpha$ index), defined as the value below which the average different of the values of $STL_{max}$ in the corresponding time window is not significantly different from 0 (p>0.01). When the average T-index of a group of selected sites became less than the $T_\alpha$ index, the group was considered to be entrained.

The objective of the automated seizure warning system is to detect preictal transitions in order to prospectively warn of an impending seizure. A seizure warning can be generated when the preictal transition is detected. The onset of the preictal transition is defined as that point in time when at least one of the monitored groups of critical electrode sites is entrained. That is, the average T-indexed for that group of sites initially above 5 (disentrained) drops to a value of, for example, 2.662 or less (entrained). These critical values were selected based on the following statistical considerations: when the T-index is greater than 5, the average $STL_{max}$ values for electrode pairs are highly significantly different (p-value <0.00001); when the T-index is less than 2.662, the average $STL_{max}$ values for electrode pairs are not significantly different (p value >0.01). Other, different critical values can alternatively be selected and used. Following each new seizure, new groups of critical electrode sites were reselected or identified and the algorithm was repeated.

To test the algorithm, a warning was considered to be true if a seizure occurred within three hours after an entrainment transition was detected. Periods different from three hours can alternatively be selected as threshold values for evaluating truthfulness of seizure warnings. If no seizure occurred within the time period from the warning, then the warning was considered to be false. If a seizure occurred without warning, then the algorithm was deemed to have failed to detect that impending seizure. Thus, the sensitivity was defined as the total number of seizures accurately predicted, divided by the total number of seizures recorded. The false prediction rate was defined as the average number of false warnings per hour.

Figure 3:
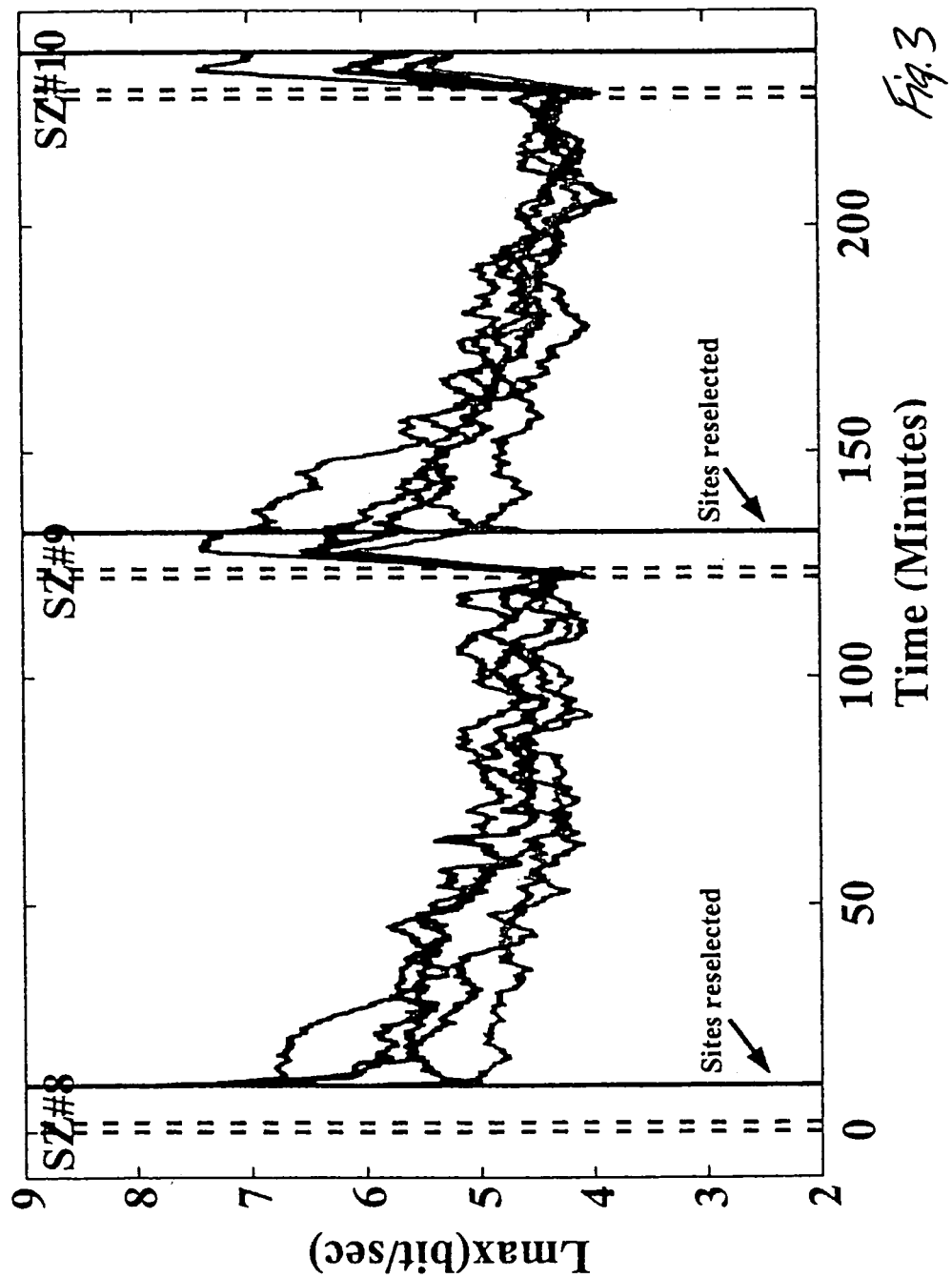
FIG. 3 illustrates an exemplary intracranial EEG recording containing three complex partial seizures.
Figure 4:
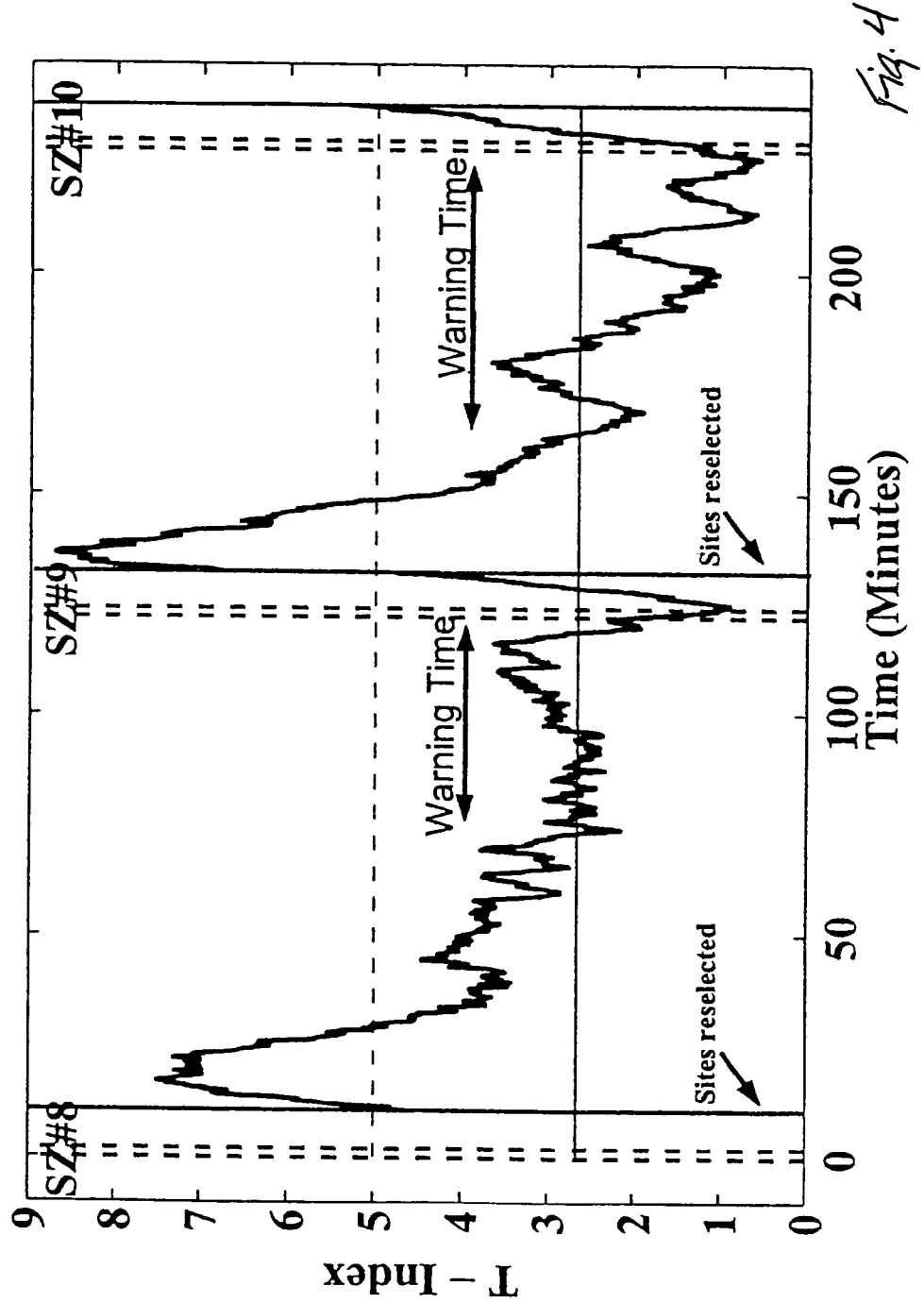
FIG. 4 illustrates an exemplary average T-index profile calculated from the $STL_{max}$ profiles shown in FIG. 3.

FIG. 3 illustrates an example of $STL_{max}$ profiles versus time, derived from EEG signals recorded from 5 critical electrode sites. These sites, selected from or identified based on, the first seizure in the series, diverge with respect to the values $STL_{max}$ after that seizure and converge to a common value prior to the next seizure (preictal transition). After occurrence of the second seizure, reselection of critical sites was made. Preictal transition and postictal divergence are reflected in the corresponding average T-index curves with the gradual reduction preictally and more rapid rise postictally, as shown in FIG. 4. This sequence of dynamical state transitions is repeated after each seizure.

Figure 5:
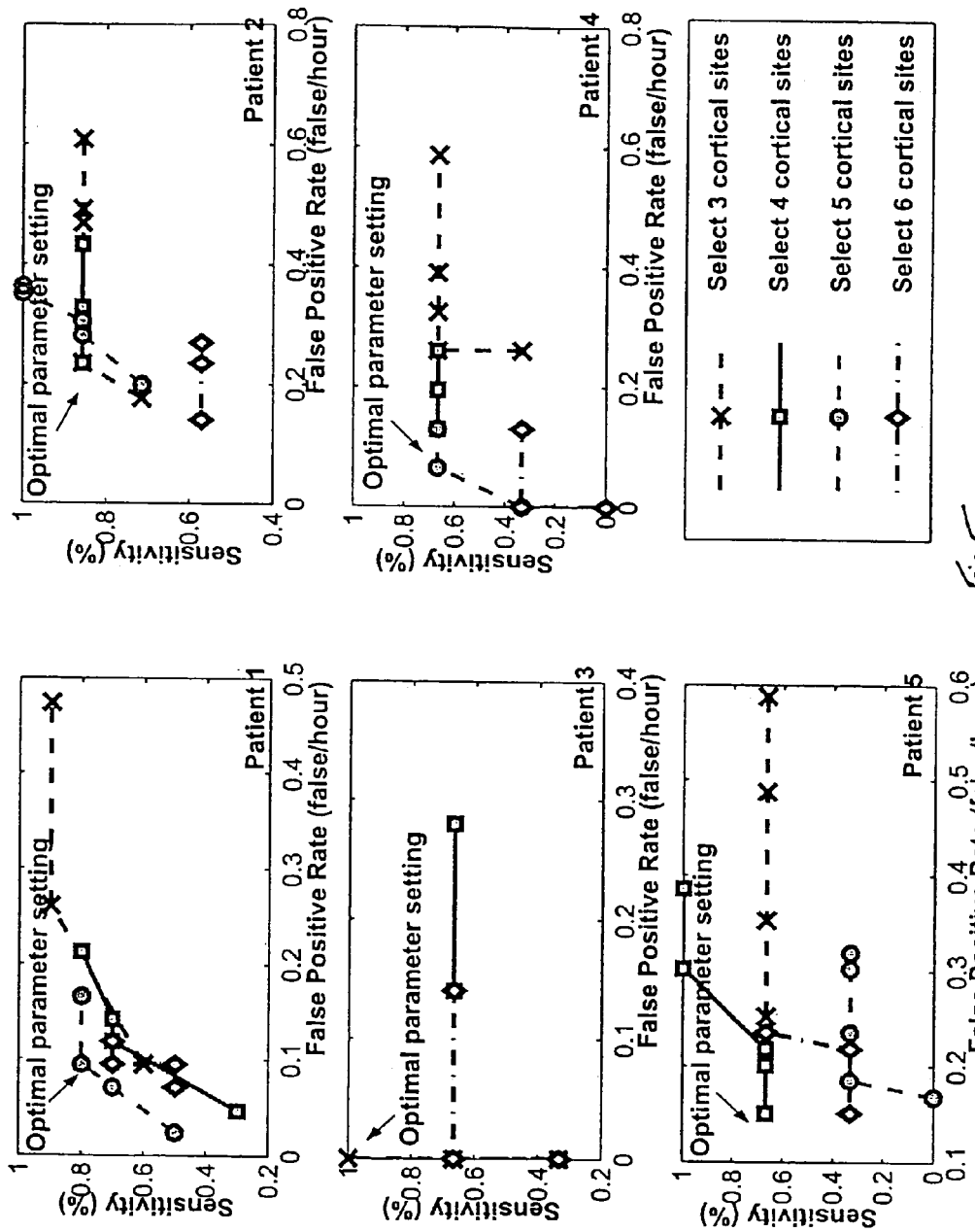
FIG. 5 illustrates performance curves for training datasets with respect to five different patients, in accordance with an exemplary method.

The algorithm was first applied in the training seizure set for each patient to determine the optimal parameter (k and m) settings. FIG. 5 shows the ROC curve of each of the five patients. Table 2 below summarizes the optimal parameter settings and their seizure warning performance.

TABLE 2

| Patient | Number of analyzed seizures | Number of critical electrodes in each group | Number of selected or identified critical groups | Sensitivity | False prediction rate (false per hour) | Average Warning Time (minutes) |
|---|---|---|---|---|---|---|
| 1 | 11 | 5 | 3 | 80.00% (8/10) | 0.095 (4/46.248) | 67.8 + 20.9 |
| 2 | 8 | 3 | 2 | 85.71% (6/7) | 0.234 (20/85.468) | 66.2 + 15.7 |
| 3 | 4 | 3 | 4 | 100% (3/3) | 0.000 (0/7.140) | 71.5 + 12.3 |
| 4 | 4 | 5 | 2 | 66.67% (2/3) | 0.065 (1/15.328) | 39.0 + 20.4 |
| 5 | 4 | 4 | 1 | 66.67% (2/3) | 0.151 (9/59.565) | 72.7 + 47.8 |
| All | 31 | | | 80.77 (21/26) | 0.159 (34/213.749) | 63.44 + 6.22 |

The criterion for determining the optimal parameter settings is that, for patients 1 and 2 with larger numbers of training seizures (10, 7 respectively), the sensitivity can be larger than 80% with the minimum false positive rate per hour. For patients 3, 4 and 5, due to the small number of training seizures (3 each), the sensitivity can be at least ⅔ with the minimum false positive rate per hour. In these five training sets, the percentage of seizures that were correctly predicted ranged from ⅔ to 100%, with an overall sensitivity of 80.77%, as shown in Table 2. The false warnings occurred at a rate ranging from 0.00 to 0.234 (overall 0.159) false warnings per hour. This corresponds, on average, to a false warning every 6.3 hours. Table 3 below summarizes the performance of the algorithm in the five testing seizure sets when using the selection parameters from the training seizure sets.

TABLE 3

| Patient | Number of analyzed seizures | Sensitivity | False Prediction Rate (false/hour) | Average warning time (minutes) |
|---------|-----------------------------|-------------|------------------------------------|--------------------------------|
| 1 | 10 | 88.89% (8/9) | 0.049 (2/41.134) | 79.3 ± 13.2 |
| 2 | 8 | 85.71% (6/7) | 0.366 (20/54.685) | 90.2 ± 19.2 |
| 3 | 3 | 100.00% (2/2) | 0.137 (1/7.278) | 79.9 ± 6.2 |
| 4 | 4 | 100.00% (3/3) | 0.178 (19/106.59) | 108.8 ± 7.4 |
| 5 | 4 | 100.00% (3/3) | 0.100 (1/9.967) | 104.9 ± 21.1 |
| All | 31 | 91.67% (22/24) | 0.196 (43/219.654) | 92.6 ± 6.2 |

As shown in Table 3, the prediction sensitivity ranged from 85.71% to 100% with an overall sensitivity of 91.67%. The false warning rates ranged from 0.049 to 0.366 (overall, 0.196) false warnings per hour. This corresponds, on average, to one false warning every 5.1 hours.

Figure 6:
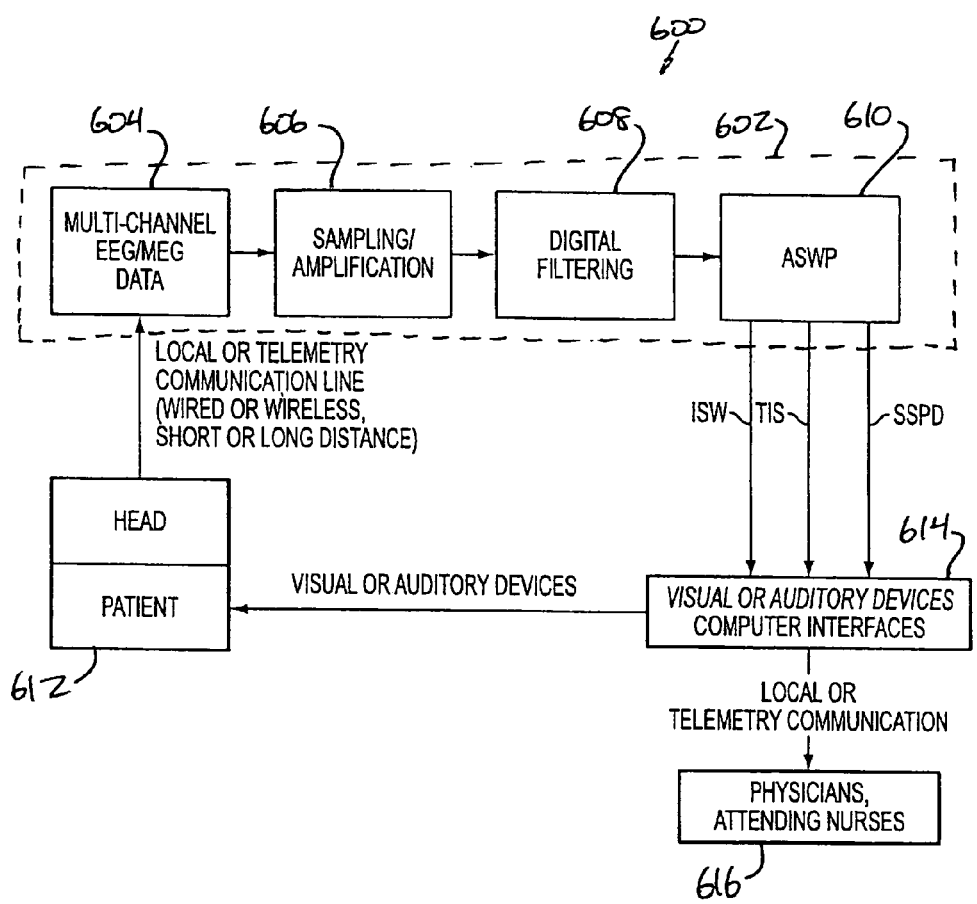
FIG. 6 illustrates an on-line system that can incorporate exemplary embodiments and methods.

FIG. 6 illustrates a block diagram of an on-line system 600 in accordance with exemplary embodiments of the invention. FIG. 6 also shows a patient 612 being monitored by the system 600, and professional staff 616 such as physicians and attending nurses to whom the system 6000 provides information. The on-line system 600 can incorporate the various features of the present invention described herein. As shown in FIG. 6, the system includes a signal processing unit 602 that receives EEG (electroencephalogram) and/or MEG (magnetoencephalogram) signals originating from the patient's head, which can for example be provided by a wire or wireless link using electrically conductive wires bearing electrical signals, optical fibers bearing light signals, a wireless link using radio frequency signals, a infrared optical link, or any other wired or wireless communication or data transmission link. The data are received by an element 604 within the processing unit, then passed to a unit 606 for sampling and amplification, then passed to a unit 608 for digital filtering, and then passed to a unit 610 that applies an algorithm capable of providing seizure warning and prediction (ASWP).

The techniques and algorithms described herein regarding signal processing, for example those shown in FIG. 2 and described in detail herein, can be performed within one or both of the units 608, 610 of the signal processor 602. The signal processor 602 can be a microprocessor, computer or computer system, and can be implemented in a central fashion or in a distributed fashion with centralized or distributed computing resources. Based on analysis of the patient's data, the unit 610 can provide signals to interface devices 614 and thereby convey results of the analysis to the professional staff 616. The signals to the interface devices can include indications of impending seizure warning (ISW), seizure susceptibility period detection (SSPD), and time to impending seizure prediction (TISP). As shown in FIG. 6, the interface devices 614 can be local to the professional staff 616, or can be remote from the staff 616 so that the signals are conveyed by intermediate devices or mechanisms via wired or wireless communication systems such as cables, the Internet, radio networks, and so forth.

The on-line system 600 may be used in any number of clinical or non-clinical applications, including diagnostic applications, as well as applications relating to patient treatment. For example, the on-line system may be used to collect and process EEG (electroencephalogram) or MEG (magnetoencephalogram) signals for subsequent clinical interpretation (e.g., to analyze and determine seizure propagation patterns). The on-line system may also be used to alert hospital or clinic staff members of an impending seizure, via a local or telemetry link, so that staff members have adequate time to prevent patient injury or provide timely medical intervention to prevent the seizure itself; to observe the seizure; or to prepare for and administer other procedures that must be accomplished during the seizure, such as the administration of radio-labelled ligands or other substances required to obtain ictal SPECT (Single Photon Emission Computed Tomography), ictal FMRI (Functional Magnetic Resonance Imaging), or ictal PET (Positron Emission Tomography) images for pre-surgical diagnostic purposes.

Thus, the methods, logics, and techniques described herein can be implemented in one or more of hardware, firmware, and software. In addition, those skilled in the art will appreciate that the methods or processes, logics, elements and techniques described herein can be implemented using a microprocessor, computer, or any other computing device, and can be implemented in one or more of hardware, firmware and software, in a single physical location or in distributed fashion among various locations or host computing platforms. Agents can be implemented in hardware and/or software or computer program(s) at any desired or appropriate location. Software can be implemented in a variety of programming styles (for example Structured Programming, Object-Oriented Programming, and so forth) and in a variety of different programming languages (for example Java, C, C++, C#, Pascal, Ada, and so forth). Those skilled in the art will also appreciate that software or computer program(s) can be stored on a machine-readable medium, wherein the software or computer program(s) includes instructions for causing a computing device such as a computer, computer system, microprocessor, or other computing device, to perform the methods or processes.

It will be appreciated by those skilled in the art that the present invention can be embodied in other specific forms without departing from the spirit or essential characteristics thereof, and that the invention is not limited to the specific embodiments described herein. The presently disclosed embodiments are therefore considered in all respects to be illustrative and not restrictive. The scope of the invention is indicated by the appended claims rather than the foregoing description, and all changes that come within the meaning and range and equivalents thereof are intended to be embraced therein.

What is claimed is:

1. A computer-implemented method for predicting an impending seizure, comprising:
   receiving dynamical measurement data regarding the system;
   applying a quadratically constrained quadratic 0-1 program to identify data components among the received data, wherein the applying comprises linearizing the quadratically constrained quadratic 0-1 program, and wherein the linearizing comprises introducing a new 0-1 variable for each product of two variables and then formulating the quadratically constrained quadratic 0-1 program as a linear 0-1 problem;

storing the identified data components; and predicting an impending seizure based on the identified data components.

2. A computer-implemented method for predicting an impending seizure, comprising:

receiving dynamical measurement data regarding the system;

applying a quadratically constrained quadratic 0-1 program to identify data components among the received data, wherein the applying comprises linearizing the quadratically constrained quadratic 0-1 program and comparing measures of statistical distance between mean values of the dynamical measurement data;

storing the identified data components; and predicting an impending seizure based on the identified data components.

3. A computer-implemented method for predicting an impending seizure, comprising:

receiving dynamical measurement data regarding the system, wherein the dynamical measurement data includes maximum Lyapunov exponents;

applying a quadratically constrained quadratic 0-1 program to identify data components among the received data, wherein the applying comprises linearizing the quadratically constrained quadratic 0-1 program;

storing the identified data components; and predicting an impending seizure based on the identified data components.

4. The method of claim 3, wherein the applying comprises applying a T-statistic to the dynamical measurement data.

5. A computer-implemented method for predicting an impending seizure, comprising:

receiving dynamical measurement data regarding the system;

applying a quadratically constrained quadratic 0-1 program to identify data components among the received data, wherein the applying comprises minimizing statistical distances between mean values of the dynamical measurement data;

storing the identified data components; and predicting an impending seizure based on the identified data components.

6. The method of claim 1, wherein the dynamical measurement data comprise multi-dimensional time series data.

7. A computer-implemented method for predicting an impending seizure, comprising:

receiving dynamical measurement data regarding the system;

applying a quadratically constrained quadratic 0-1 program to identify data components among the received data, wherein the applying comprises applying Karush Kuhn optimality conditions and then formulating the quadratically constrained quadratic 0-1 program as a linear mixed integer 0-1 problem;

storing the identified data components; and predicting an impending seizure based on the identified data components.

8. The method of claim 7, comprising displaying the predicted future behavior.

9. The method of claim 7, wherein the applying comprises comparing measures of statistical distance between mean values of the dynamical measurement data.

10. The method of claim 7, wherein the dynamical measurement data includes maximum Lyapunov exponents.

11. The method of claim 10, wherein the applying comprises applying a T-statistic to the dynamical measurement data.

12. A computer-implemented method for predicting an impending seizure, comprising:

receiving dynamical measurement data regarding the system, wherein the receiving comprises receiving largest Lyapunov exponent (STLmax) values calculated based on multi-channel data signals recorded from a brain;

applying a quadratically constrained quadratic 0-1 program to identify data components among the received data;

storing the identified data components; and predicting an impending seizure based on the identified data components.

13. The method of claim 12, wherein the applying comprises applying the quadratically constrained quadratic 0-1 program to profiles of the calculated STLmax values to identify critical, data channels recorded from a brain area.

14. The method of claim 13, further comprising:

monitoring a T-index profile of the identified critical data channels; and warning of the impending seizure, based on the monitoring.

15. The method of claim 13 wherein the applying comprises linearizing the quadratically constrained quadratic 0-1 program, wherein the linearizing comprises introducing a new 0-1 variable for each product of two variables and then formulating the quadratically constrained quadratic 0-1 program as a linear 0-1 problem.

16. The method of claim 13, wherein the applying comprises applying Karush-Kuhn optimality conditions and then formulating the quadratically constrained quadratic 0-1 program as a linear mixed integer 0-1 problem.

17. The method of claim 13, wherein the identifying comprises minimizing statistical distances between mean values and/or other synchronization degrees of the calculated STLmax values.

18. The method of claim 13, wherein the applying comprises comparing measures of statistical distance between mean values and/or other synchronization degrees of the calculated STLmax values.

* * * * *

UNITED STATES PATENT AND TRADEMARK OFFICE
CERTIFICATE OF CORRECTION

PATENT NO. : 7,461,045 B1  
APPLICATION NO. : 10/920446  
DATED : December 2, 2008  
INVENTOR(S) : Chaovalitwongse et al.

It is certified that error appears in the above-identified patent and that said Letters Patent is hereby corrected as shown below:

Column 1, line 19, after "EB002089." please add

--The United States Government has certain rights in the invention.--

Signed and Sealed this

Twenty-fourth Day of March, 2009

JOHN DOLL  
*Acting Director of the United States Patent and Trademark Office*